(12) United States Patent
Marczyk

(10) Patent No.: US 7,431,188 B1
(45) Date of Patent: Oct. 7, 2008

(54) SURGICAL STAPLING APPARATUS WITH POWERED ARTICULATION

(75) Inventor: Stanislaw Marczyk, Stratford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 18 days.

(21) Appl. No.: 11/724,733

(22) Filed: Mar. 15, 2007

(51) Int. Cl.
*A61B 17/068* (2006.01)

(52) U.S. Cl. ............... 227/175.1; 227/19; 606/139; 606/219

(58) Field of Classification Search ............ 227/19, 227/178, 176, 175.1, 176.1, 180.1, 175.2; 606/139, 219
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 3,949,924 A * | 4/1976 | Green | 227/132 |
| 4,204,623 A * | 5/1980 | Green | 227/19 |
| 4,429,695 A | 2/1984 | Green | |
| 5,040,715 A | 8/1991 | Green et al. | |
| 5,065,929 A | 11/1991 | Schulze et al. | |
| 5,307,976 A * | 5/1994 | Olson et al. | 227/175.3 |
| 5,312,023 A | 5/1994 | Green et al. | |
| 5,318,221 A | 6/1994 | Green et al. | |
| 5,326,013 A | 7/1994 | Green et al. | |
| 5,332,142 A | 7/1994 | Robinson et al. | |
| 5,356,064 A * | 10/1994 | Green et al. | 227/177.1 |
| 5,381,943 A | 1/1995 | Allen et al. | |
| 5,431,323 A | 7/1995 | Smith et al. | |
| 5,467,911 A * | 11/1995 | Tsuruta et al. | 227/175.1 |
| 5,485,947 A * | 1/1996 | Olson et al. | 227/176.1 |
| 5,560,532 A * | 10/1996 | DeFonzo et al. | 227/176.1 |
| 5,575,799 A | 11/1996 | Bolanos et al. | |
| 5,607,095 A | 3/1997 | Smith et al. | |
| 5,669,544 A * | 9/1997 | Schulze et al. | 227/176.1 |
| 5,673,841 A * | 10/1997 | Schulze et al. | 227/175.1 |
| 5,692,668 A * | 12/1997 | Schulze et al. | 227/175.1 |
| 5,829,662 A | 11/1998 | Allen et al. | |
| 5,855,311 A * | 1/1999 | Hamblin et al. | 227/176.1 |
| 5,865,361 A * | 2/1999 | Milliman et al. | 227/176.1 |
| 5,897,562 A * | 4/1999 | Bolanos et al. | 606/139 |
| 6,241,139 B1 * | 6/2001 | Milliman et al. | 227/175.1 |
| 6,669,073 B2 * | 12/2003 | Milliman et al. | 227/175.2 |
| 6,953,139 B2 * | 10/2005 | Milliman et al. | 227/175.1 |
| 6,959,852 B2 * | 11/2005 | Shelton et al. | 227/182.1 |
| 6,981,628 B2 | 1/2006 | Wales | |
| 7,083,075 B2 * | 8/2006 | Swayze et al. | 227/176.1 |

(Continued)

FOREIGN PATENT DOCUMENTS

WO    WO 03/030743 A2    10/2002

*Primary Examiner*—Scott A. Smith

(57) ABSTRACT

The surgical stapling apparatus includes a handle assembly, an elongated body extending distally from the handle assembly, and an articulation mechanism for articulating a tool assembly. The articulation mechanism includes a first gear rotatably mounted on a transmission shaft and configured to engage a second gear, a clutch interconnecting the second gear and a main shaft; and a yoke shaft coupled to the main shaft and adapted to linearly advance a J-channel, the J-channel operatively connected to an articulation link. A motor assembly may rotate the transmission shaft of the articulation mechanism. Alternatively, the articulation mechanism may include an articulation knob. Users may manually rotate the articulation knob to articulate the tool assembly of the surgical stapling apparatus.

17 Claims, 11 Drawing Sheets

U.S. PATENT DOCUMENTS 7,128,254 B2 * 10/2006 Shelton et al. ........... 227/181.1
7,143,925 B2   12/2006 Shelton, IV et al.
7,303,108 B2 * 12/2007 Shelton, IV .............. 227/179.1

* cited by examiner

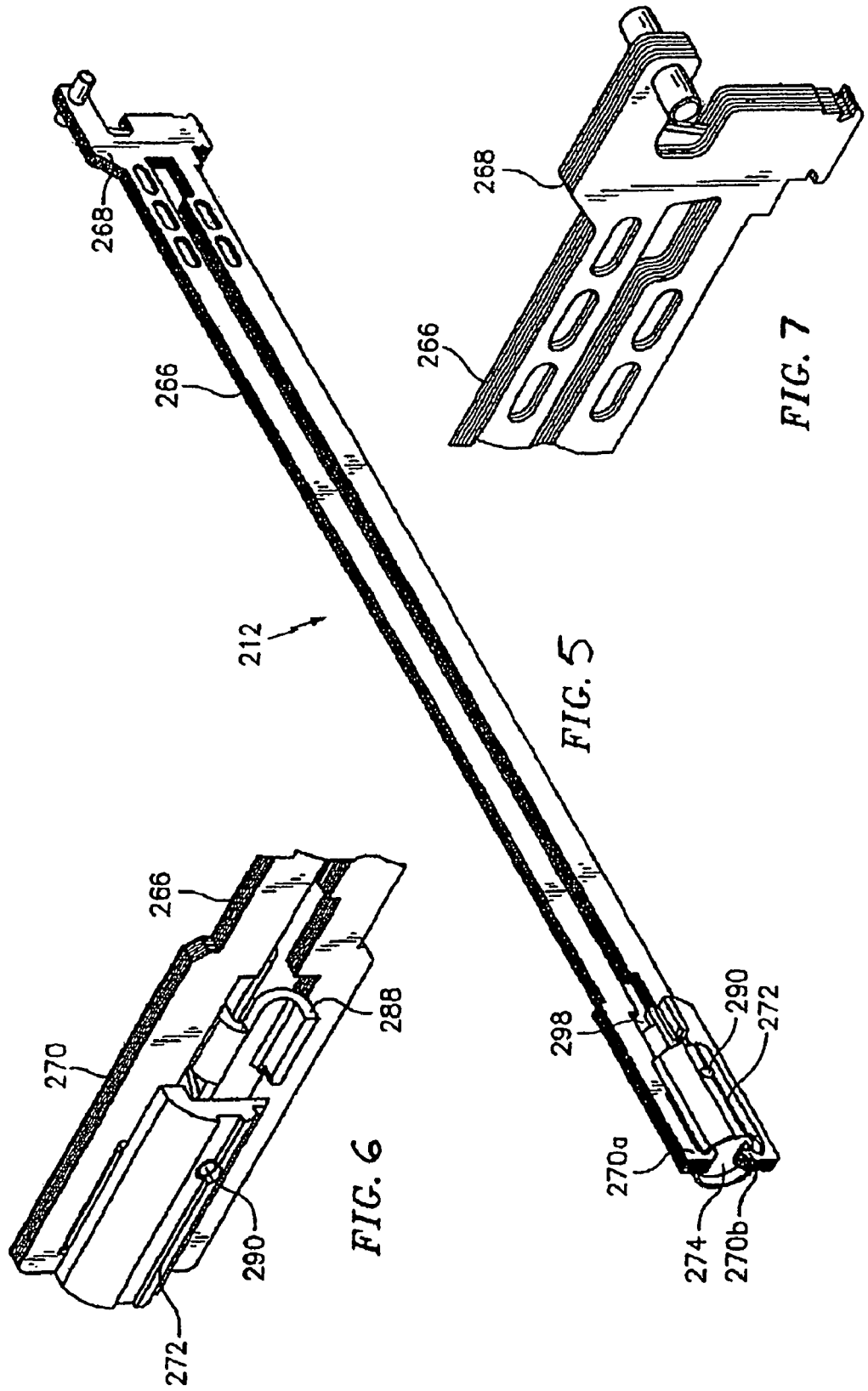

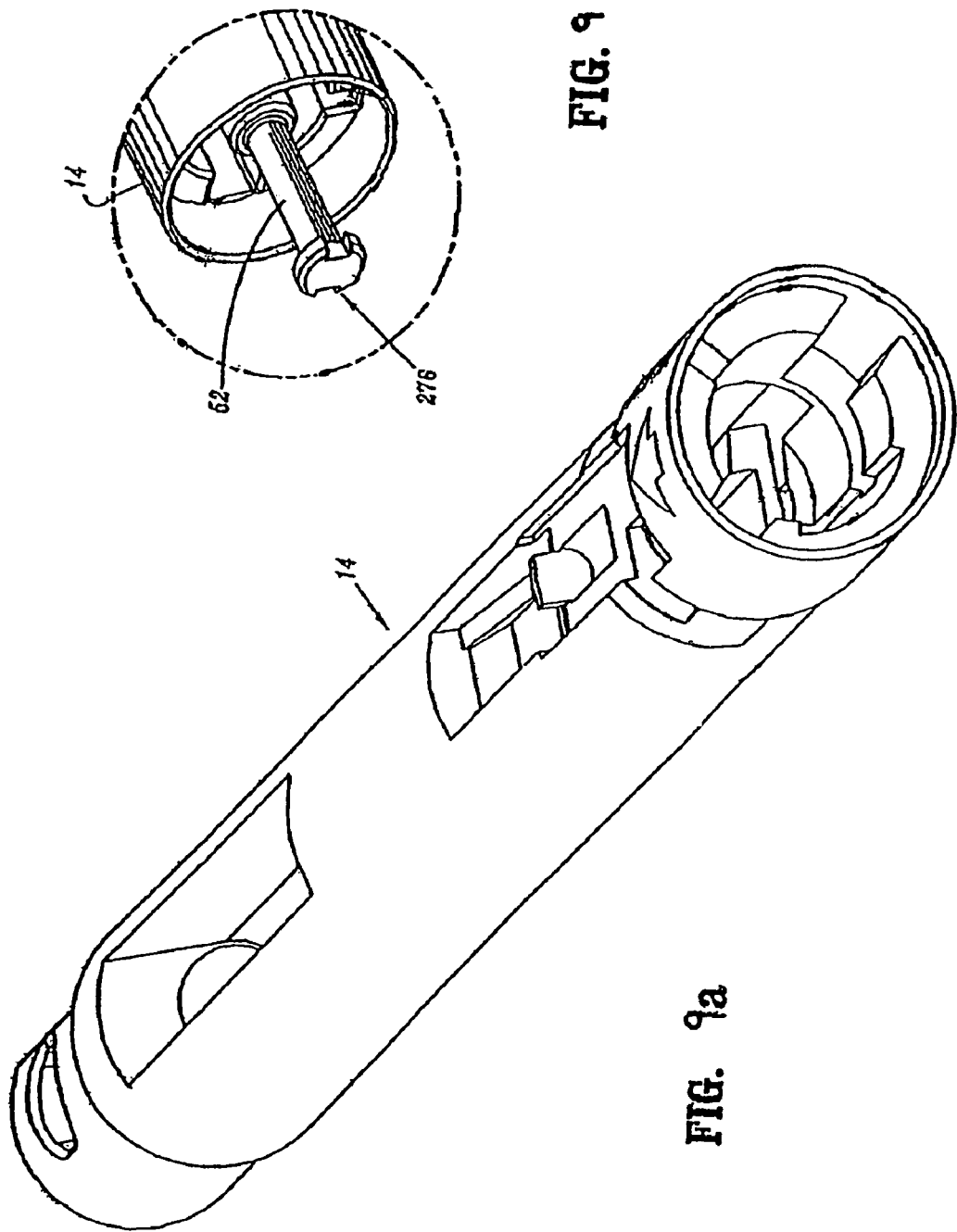

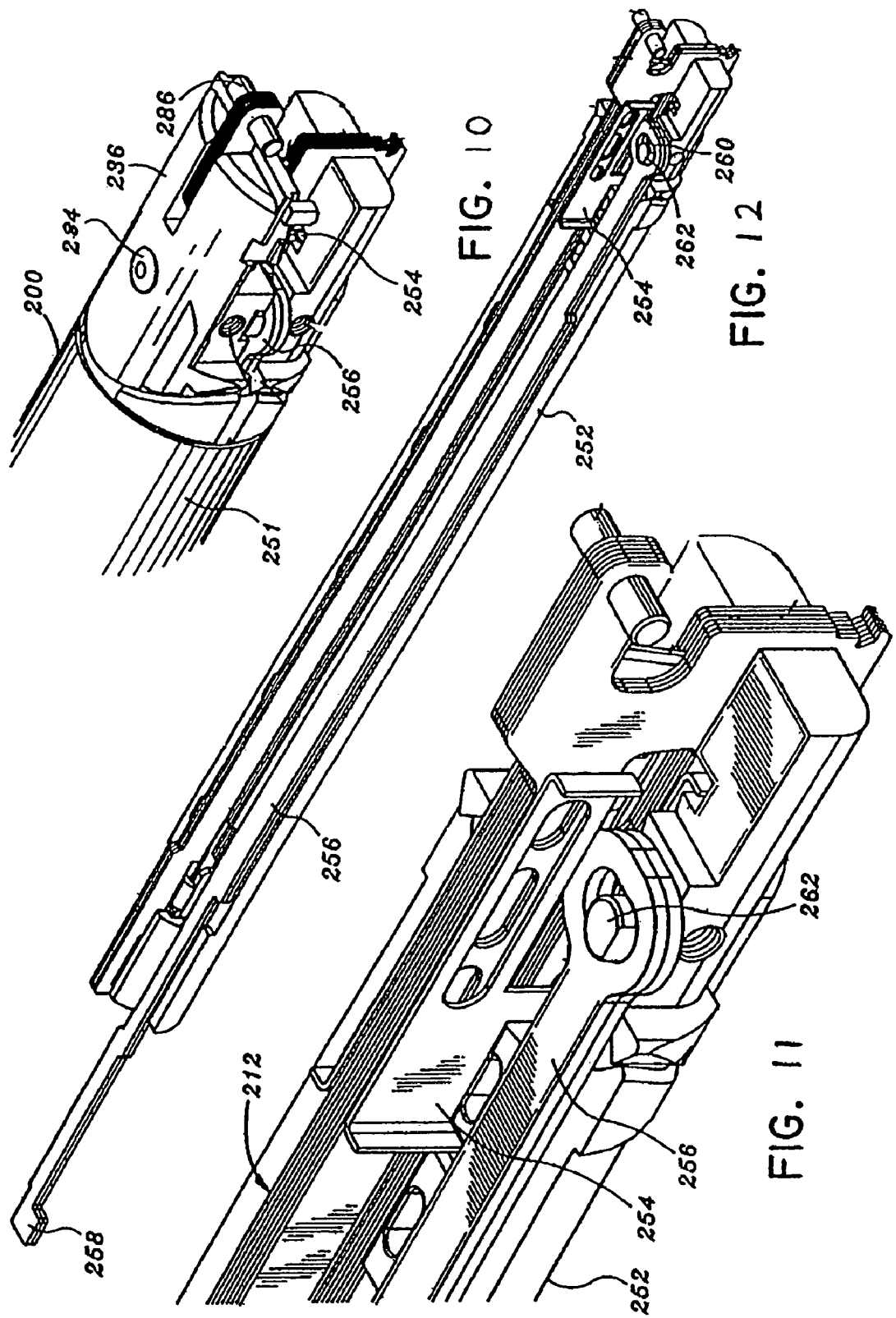

SURGICAL STAPLING APPARATUS WITH POWERED ARTICULATION

BACKGROUND

1. Technical Field

The present disclosure relates to a surgical stapling apparatus. More particularly, the present disclosure relates to an endoscopic surgical stapling apparatus that includes a mechanism for articulating a tool assembly.

2. Background of Related Art

Surgical fastening devices, such as surgical stapling apparatuses, are well known in the art. These devices typically include two elongated jaw members to capture or clamp tissue. One jaw member carries a staple cartridge that houses a plurality of staples arranged in at least two lateral rows while the other jaw member has an anvil that defines a surface for forming the staple legs as the staples are driven from the staple cartridge. For the most part, the stapling operation is effected by cam members that travel longitudinally through the staples cartridge, with the cam members actuating upon staple pushers to sequentially eject the staples from the staple cartridge. A knife may travel between the staple rows to longitudinally cut or open the stapled tissue between the rows of staples. Examples of this kind of instrument are disclosed in U.S. Pat. Nos. 3,079,606 and 3,490,675.

U.S. Pat. No. 3,499,591 also discloses a stapling apparatus with a pair row of staples on each side of the incision. The patent discloses a surgical stapler that has an upper jaw member and a lower jaw member. The upper jaw member includes a disposable cartridge while the lower jaw member contains a disposable anvil having a series of staple-closing depressions aligned with a plurality of staple-carrying grooves of the cartridge. In operation, a cam member translates through an elongated guide path between the two sets of staple-carrying grooves. Staple drive members are located within the grooves and are positioned in such a manner so as to effect ejection of the staples from the staple cartridge. Other examples of such stapling instruments are disclosed in U.S. Pat. Nos. 4,429,695 and 5,065,929.

Each of the instruments described hereinabove is designed for use in conventional surgical procedures wherein surgeons have direct manual access to the operative site. Endoscopic or laparoscopic procedures, however, are performed through a small incision or through a narrow cannula inserted through a small entrance wounds in the skin. To address the specific needs of endoscopic or laparoscopic surgical procedures, surgical stapling devices have been developed and are disclosed in, for example, U.S. Pat. Nos. 5,040,715; 5,312,023; 5,318,221; 5,326,013; 5,332,142; and 6,241,139.

Tyco Healthcare Group, LP, the assignee of the present application, has successfully manufactured and marketed endoscopic stapling instruments, such as the Multifire ENDO GIA™ 30, Multifire ENDO GIA™ 60 and Multifire ENDO TA™ 30 instruments, for a number of years. An articulating endoscopic stapler known as the ENDO GIA™ Universal stapler has also been marketed. Typically, these devices include an articulation mechanism having an articulation lever operatively engaged with a cam member having a stepped camming channel. Current stapling instruments allow manual operation of the articulation lever. These instruments have provided significant clinical benefits. Nonetheless, improvements to these instruments are still possible.

It would be desirable to provide an improved articulation mechanism for a surgical stapling apparatus. It would also be desirable to provide an articulation mechanism capable of being operated either manually or electromechanically.

Accordingly, it is an object of this disclosure to provide an improved articulation mechanism that articulates the tool assembly of a surgical stapling apparatus by electromechanical means. It also the object of this disclosure to provide an improved articulation mechanism that will allow a user to articulate with minimal effort and with only one hand the tool assembly of a surgical stapling instrument.

Another object of the disclosure is to provide an articulation mechanism capable of very accurate and fine position adjustment at a speed that can be easily controlled by a variable speed switch.

Still another object of the disclosure is to provide an articulation mechanism with a manual override for additional reliability and safety.

SUMMARY

The present disclosure describes a surgical stapling apparatus having a handle assembly, an elongated body extending distally from the handle assembly, and an articulation mechanism. The articulation mechanism may include a first gear rotatably mounted on a transmission shaft and configured to engage a second gear, a clutch interconnecting the second gear and a main shaft, and a yoke shaft coupled to the main shaft and adapted to linearly advance a J-channel operatively connected to an articulation link. The yoke shaft of the surgical stapling apparatus can include a pin slidably secured on an elongated slot of the J-channel. The J-channel, in turn, may have a projection extending therefrom. Moreover, an articulation knob operatively connected to the main shaft may be mounted on the distal end of the handle assembly.

The surgical stapling apparatus may further include a motor assembly operatively coupled to the transmission shaft. A battery pack may be positioned on the proximal end of the handle assembly to power the motor assembly. The stapling apparatus may have a switch mounted on the proximal end of the handle assembly for activating the motor assembly.

A surgeon can articulate the tool assembly of the described surgical stapling apparatus by rotating the transmission shaft. The transmission shaft may be rotated electromechanically by activating the motor assembly. Alternatively, a user may manually rotate the transmission shaft by rotating the articulation knob.

BRIEF DESCRIPTION OF THE DRAWINGS

FIG. 5 is an enlarged perspective view of the axial drive assembly;

FIG. 6 is an enlarged perspective view of the proximal end of the axial drive assembly shown in FIG. 5;

FIG. 7 is an enlarged perspective view of the distal end of the axial drive assembly of the axial drive assembly of FIG. 5;

FIG. 9 is an enlarged perspective view of the distal end of the elongated body of the stapling apparatus shown in FIG. 1;

FIG. 9a is a further enlarged perspective view of the distal end of the elongated body of FIG. 9, shown without the control rod extending therethrough;

FIG. 10 is an enlarged perspective view of the mounting assembly of the disposable loading unit shown in FIGS. 1-3 mounted to a distal end portion of the proximal housing portion;

FIG. 11 is an enlarged perspective view of the proximal housing portion and the mounting assembly of the disposable loading unit shown in FIGS. 1-3 with the upper housing half removed;

FIG. 12 is a perspective view of the proximal housing portion and the mounting assembly of the disposable loading unit shown in FIGS. 1-3 with the upper housing half removed;

DETAILED DESCRIPTION OF THE EMBODIMENTS

Figure 1:
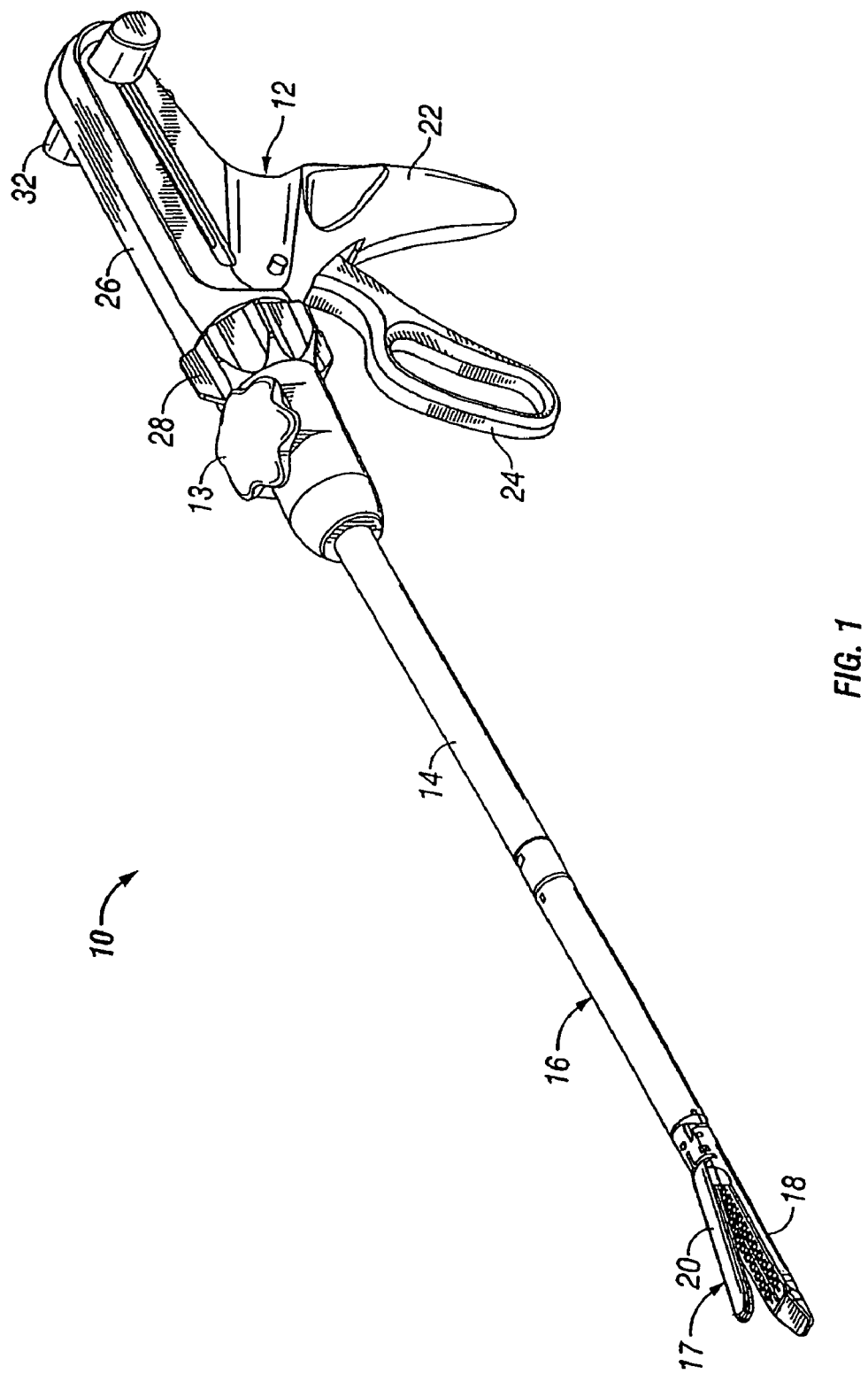
FIG. 1 is a top perspective view of an embodiment of the presently disclosed surgical stapling apparatus.

The embodiments of the present disclosure will now be described in detail with reference to the drawings, in which like reference numerals designate identical or corresponding elements in each of the several views.

In the drawings and the description that follows, the term "proximal", as is traditional, will refer to the end of the stapling apparatus which is closest to the operator, while the term "distal" will refer to the end of the apparatus which is furthest from the operator. Terms such as "above," "below," "forward," "rearward," etc. are simply used for convenience of description.

Figure 2:
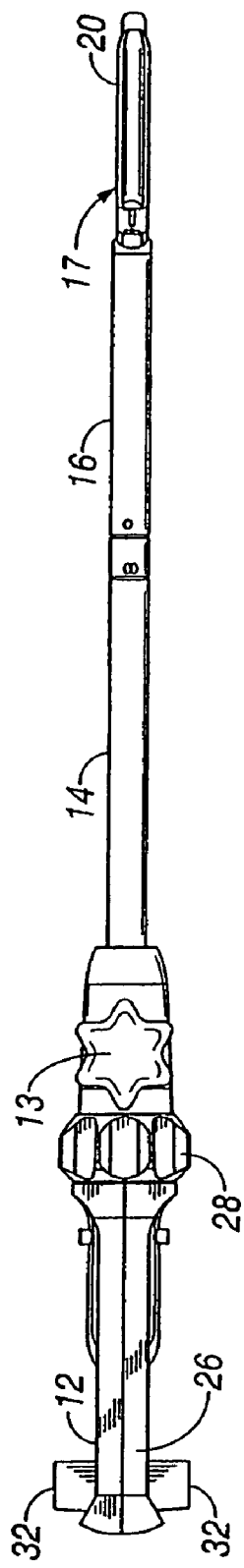
FIG. 2 is a top view of the surgical stapling apparatus shown in FIG. 1.
Figure 3:
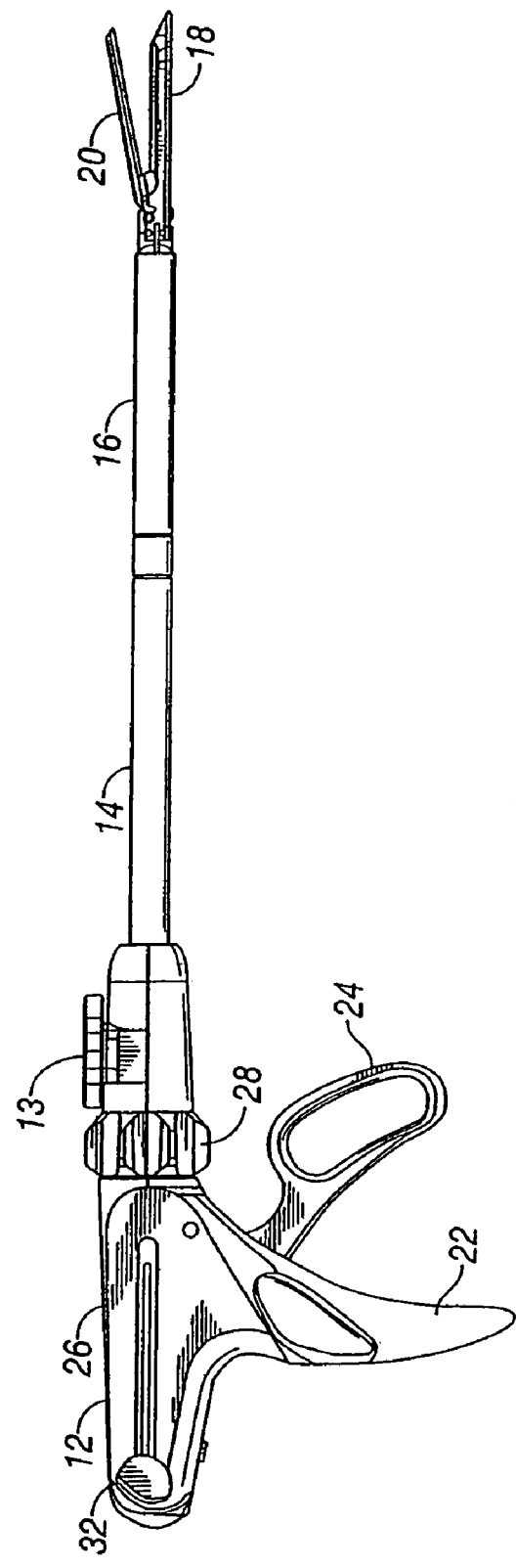
FIG. 3 is a side view of the surgical stapling apparatus shown in FIGS. 1 and 2.

FIGS. 1-3 show a surgical stapling apparatus, generally referred to as 10. In the interest of brevity, this disclosure will focus primarily on systems, methods and structures for articulating a tool assembly of surgical stapling apparatus 10. A detailed description of surgical stapling apparatus 10 is disclosed in U.S. Pat. No. 6,953,139, the entire disclosure of which is hereby incorporated by reference. Although the present disclosure is presented in the context of surgical stapling apparatus 10, the present invention is applicable to any apparatus having an articulating surgical tool.

Surgical stapling apparatus 10 is an endoscopic apparatus and includes a handle assembly 12 and an elongated body 14 extending therefrom. A loading unit which is replaceable and may be disposable, or DLU 16, is releasably secured to the distal end of elongated body 14. While the drawings illustrate a DLU 16, it is understood and within the scope of the present disclosure that a single loading unit (SULU) or other end effector can equally be used in cooperation with surgical stapling apparatus 10. DLU 16 includes a tool assembly 17 having a cartridge assembly 18 housing a plurality of surgical staples and an anvil assembly 20 movably secured in relation to cartridge assembly 18. As seen in the FIGS. 1-3, DLU 16 is configured to apply linear rows of staples. DLUs for applying any number of rows of staples, having staple pockets arranged in various patterns or DLUs and end effectors having various lengths, e.g., 30, 45 mm, or 60 mm, are also envisioned. U.S. Pat. No. 6,953,139, the disclosure of which is hereby incorporated by reference herein, includes a detailed discussion of various kinds of DLUs. A loading unit having various surgical end effectors may be used, including linear stapling tool assemblies. The linear stapling tool assemblies can include predetermined staple sizes and staple line lengths in various sizes and configurations. The stapling tool assemblies include circular, linear and other shapes.

Figure 4:
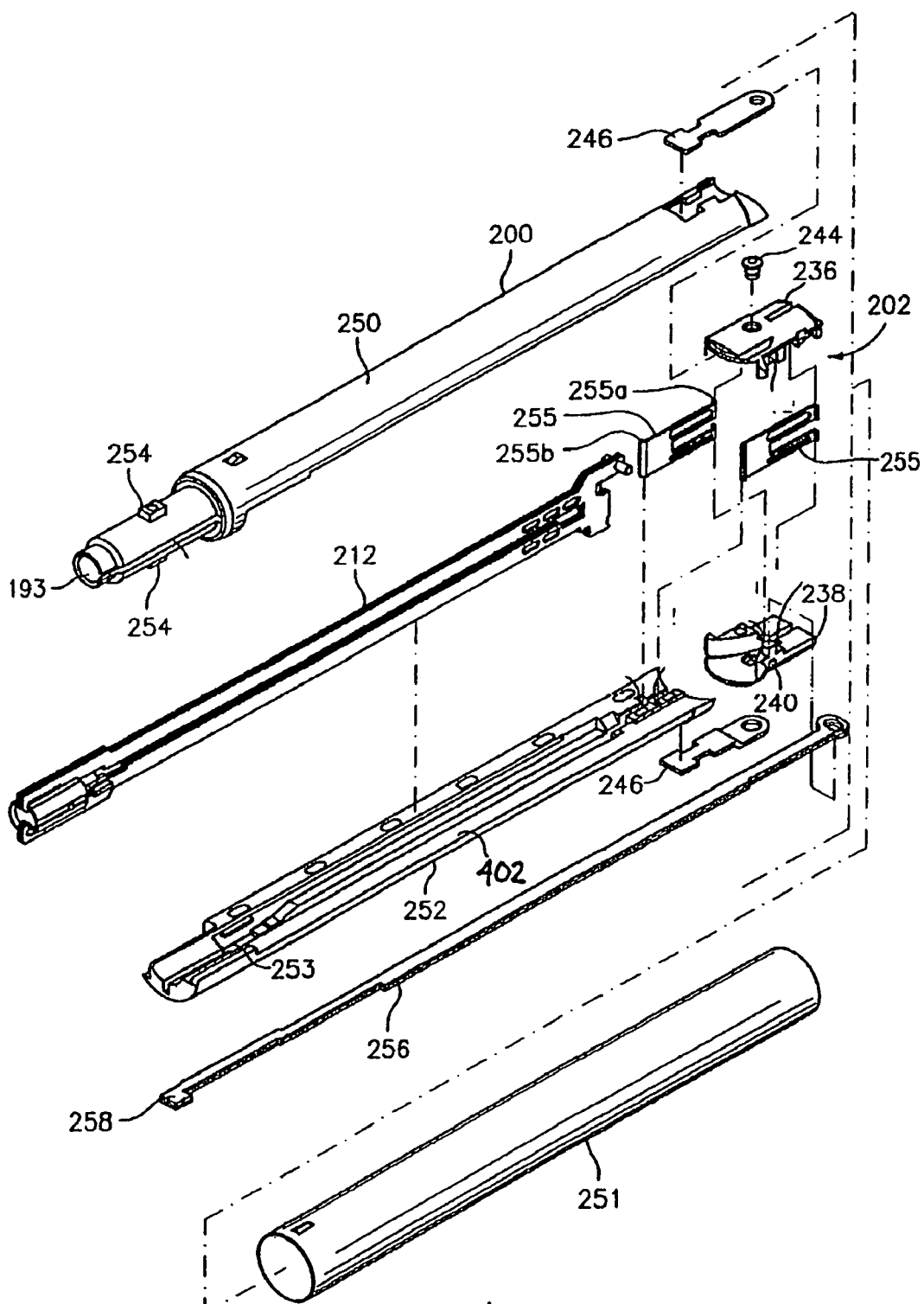
FIG. 4 is an enlarged top perspective view, with parts separated, of the proximal housing portion and mounting assembly of the DLU shown in FIGS. 1-3.
Figure 8:
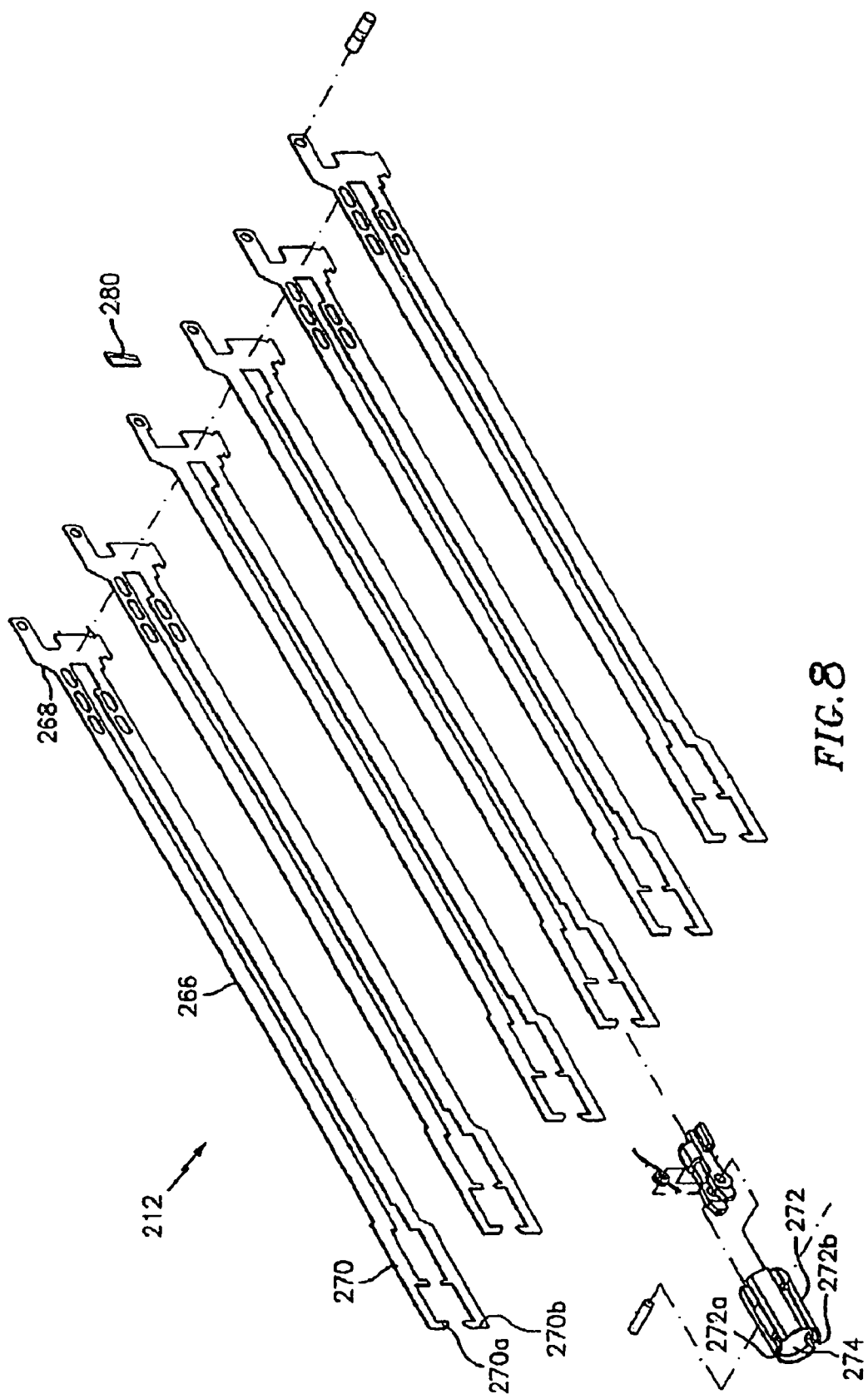
FIG. 8 is a perspective view with parts separated of the axial drive assembly.

With reference to FIG. 4, DLU 16 includes a mounting assembly 202. Mounting assembly 202 includes an upper and a lower mounting portion 236, 238, respectively. A centrally located pivot member 244 extends from each of upper and lower mounting portions 236, 238 via a pair of coupling members 246. Coupling members 246 each include an interlocking proximal portion 248 configured to be received in grooves 290 formed in the proximal end of upper and lower housing halves 250, 252 to retain mounting assembly 202 and upper and lower housing halves 250, 252 in a longitudinally fixed position in relation to each other.

Upper housing half 250 and lower housing half 252 are contained within an outer sleeve, shell or casing 251. The proximal end of upper housing half 250 includes an insertion tip 193 extending proximally therefrom. Insertion tip 193 includes engagement nubs 254, preferably a pair of diametrically opposed engagement nubs 254, extending radially outwardly therefrom, for releasably engaging the distal end of body 14. Nubs 254 form a bayonet-type coupling with the distal end of body 14. Housing halves 252 and 252 define a channel 253 for slidably receiving axial drive assembly 212 therein. A second articulation link 256 is dimensioned to be slidably positioned within a slot 402 formed in upper and lower housing halves 250, 252. A pair of blow out plate assemblies 255 are positioned adjacent the distal end of housing portion 200 adjacent the distal end of axial drive assembly 212 to prevent outward buckling and bulging of drive assembly 212 during articulation and firing of surgical stapling apparatus 10. For a detailed discussion of the structure and operation of blow out plate assemblies 255, reference is made to International Application Serial No. PCT/US02/32031, filed on Oct. 4, 2002, entitled "Surgical Stapling Device", the entire contents of which are herein incorporated by reference.

With reference to FIGS. 4-8, axial drive assembly 212 includes an elongated drive beam 266 including a distal working head 268 and a proximal engagement section 270. Drive beam 266 may be constructed from a single sheet of material or, preferably, multiple stacked sheets, as shown in FIG. 1. Engagement section 270 includes a pair of resilient engagement fingers 270a and 270b which are dimensioned and configured to mountingly engage a pair of corresponding retention slots 272a and 272b formed in drive member 272. Drive member 272 includes a proximal porthole 274 configured to receive distal end 276 of a drive member, e.g., drive rod or control rod 52 (FIG. 9) when the proximal end of DLU 16 is being engaged with elongated body 14 of surgical stapling apparatus 10. Control rod 52 functions to impart axial movement of drive assembly 212 from handle assembly 12.

In one embodiment, optionally, a locking member may be supported on engagement section 270 of axial drive assembly 212. In operation, when axial drive assembly 212 is actuated, by applying a predetermined force to movable handle member 24 to advance axial drive assembly 212 distally, the locking member provides an audible and tactile indication that surgical stapling apparatus 10 has been actuated. For a detailed discussion of the structure and operation of the locking member, reference is made to the aforementioned International Application Serial No. PCT/US02/32031, the disclosure of which is hereby incorporated by reference herein. The locking member may also prevent inadvertent partial actuation of DLU 16, such as during shipping, by locking axial drive assembly 212 at a fixed position within DLU 16 until a predetermined axial force has been applied to axial drive assembly 212.

Handle assembly 12 includes a stationary handle member 22, a movable handle member 24, and a barrel portion 26. A rotatable member 28 may be mounted on the distal end of barrel portion 26 to facilitate rotation of elongated body 14 with respect to handle assembly 12. Two retraction knobs 32 are movably positioned along barrel portion 26 to return surgical stapling apparatus 10 to a retracted position. An articulation knob 13 is mounted on the distal end of barrel portion 26 such as on rotatable knob 28 to facilitate articulation of tool assembly 17. The operation of the articulation knob 28 and its operative structure is set forth in detail in U.S. patent application Ser. No. 11/544,203, the contents of which are hereby incorporated herein by reference.

Referring to FIGS. 10-12, second articulation link 256 includes at least one elongated metallic plate. Two or more metallic plates may be stacked to form link 256. The proximal end of second articulation link 256 includes a hook portion 258 configured to engage a first articulation link, which extends through the elongated body 14, and the distal end of the second articulation link 256 includes a loop 260 dimensioned to engage a projection 262 formed on mounting assembly 202. Projection 262 is laterally offset from pivot member 244 such that linear movement of second articulation link 256 causes mounting assembly 202 to pivot about pivot members 244 to articulate tool assembly 17.

Figure 13:
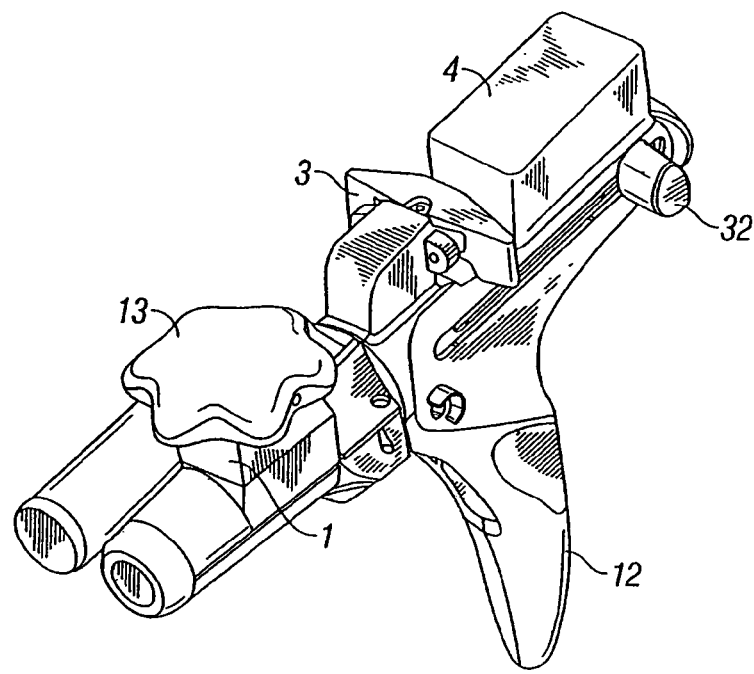
FIG. 13 is a perspective view of a handle assembly according to an embodiment of the presently disclosed surgical stapling apparatus.
Figure 14:
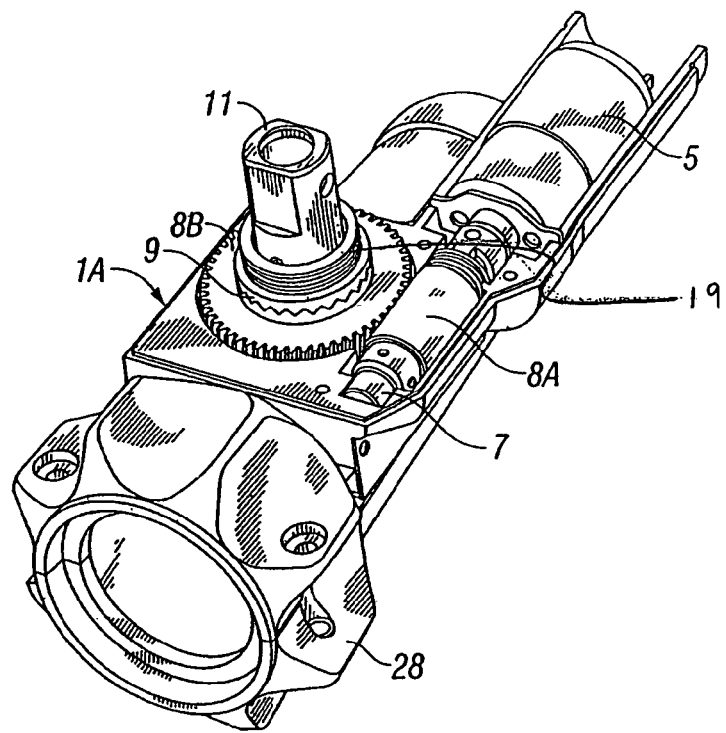
FIG. 14 is a perspective view of a portion of a handle assembly according to an embodiment of the presently disclosed surgical stapling apparatus.

Referring now to FIGS. 13 and 14, surgical apparatus 10 also includes an articulation actuation mechanism 1. Articulation actuation mechanism 1 includes an articulation knob 13 mounted adjacent to rotatable knob 28, a motor assembly 5 and a switch 3, which may be positioned on top of the handle assembly 12. Switch 3 activates and controls articulation mechanism 1 and is configured to be reached from both sides of surgical stapling apparatus 10. A battery pack 4 is situated at the handle assembly 12 for supplying power to articulation mechanism 1. It is envisioned that articulation mechanism 1 may be powered by a suitable external energy source.

Figure 15:
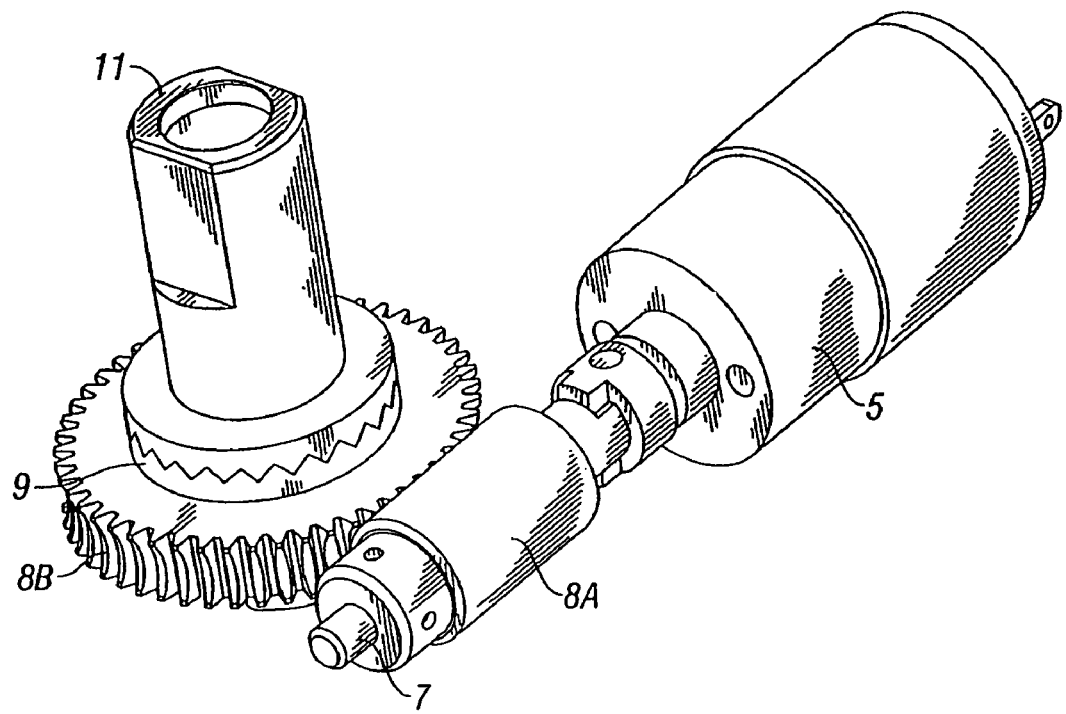
FIG. 15 is a perspective view of an articulation mechanism according to an embodiment of the presently disclosed surgical stapling apparatus.
Figure 16:
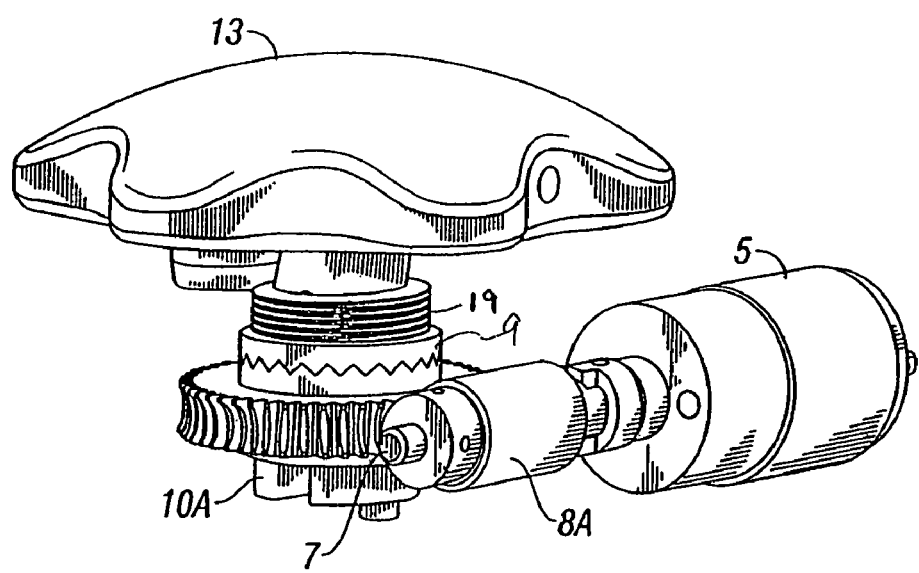
FIG. 16 is a perspective view of an articulation mechanism according to an embodiment of the presently disclosed surgical stapling apparatus.

With reference to FIGS. 15 and 16, motor assembly 5 is supported within rotatable knob 28 and is operatively connected to a rotating transmission shaft 7. A first gear 8a is mounted on transmission shaft 7 so that at least a portion of first gear 8a surrounds transmission shaft 7. First gear 8a has at least one tooth and, desirably, a plurality of teeth. A second gear 8b is configured to engage first gear 8a and thereby reduce the rotational speed produced by motor assembly 5. It is contemplated that any suitable speed reducing means known in the art may be employed with the articulation mechanism 1 in lieu of gears 8a, 8b. Second gear 8b is connected to a main shaft 11 by a slip clutch 9 such that rotation of second gear 8b will cause corresponding rotation of main shaft 11. Slip clutch 9 includes a first disk having teeth or grooves and a second disc having teeth or grooves. A spring 19 biases slip clutch 9 upwardly. As seen in FIG. 16, articulation mechanism 1 may include an articulation knob 13 mounted to main shaft 11. Articulation knob 13 is accessible to the user and can be manipulated to manually articulate tool assembly 17, or it may serve as an articulation position indicator.

Figure 17:
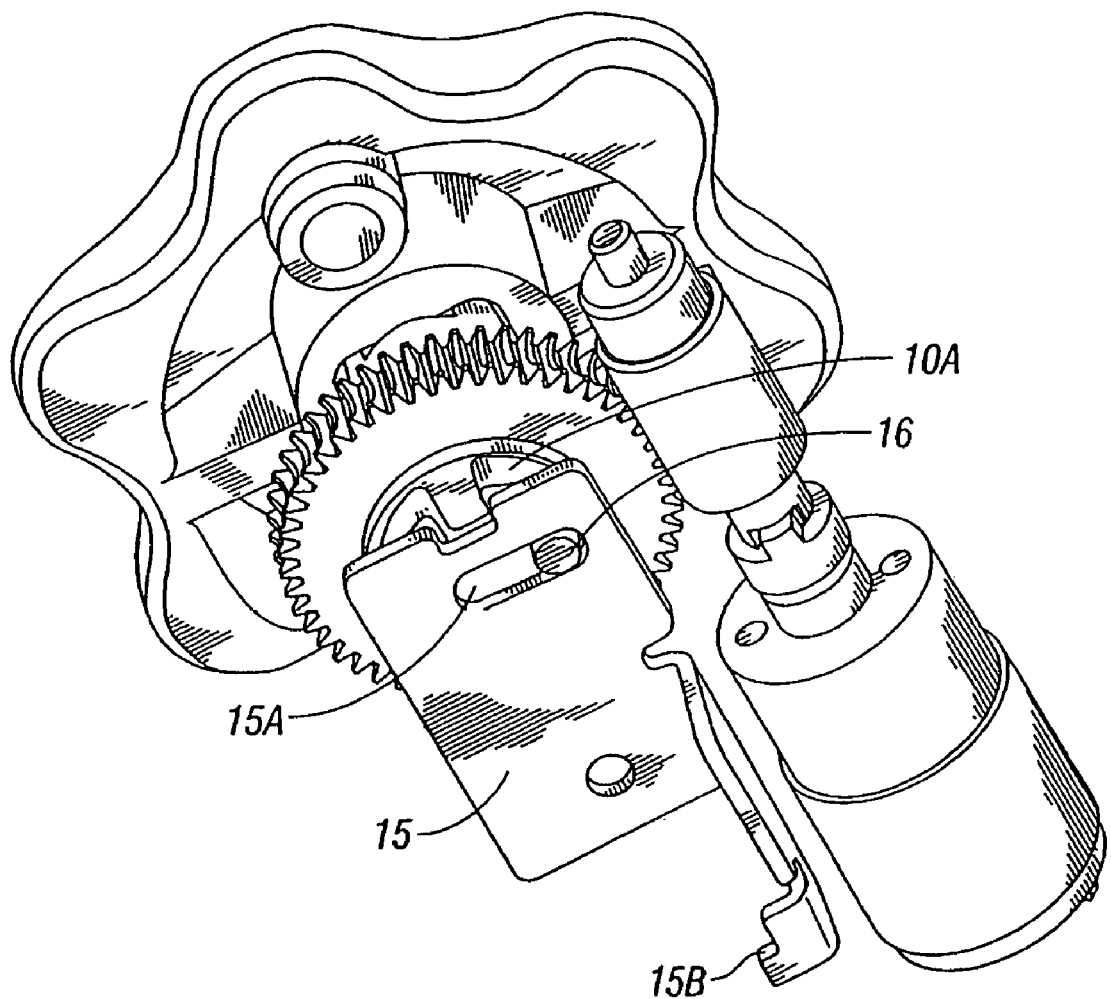
FIG. 17 is a perspective view of an articulation mechanism according to an embodiment of the presently disclosed surgical stapling apparatus.

Referring to FIG. 17, main shaft 11 is slidedably attached to a yoke shaft 10a to allow manual operation of the articulation mechanism 1, as well as to avoid overloading the motor assembly 5. Yoke shaft 10a includes a pin 16 operatively arranged with a J-channel 15. J-channel 15 includes a slot 15a for receiving the pin 16 and a projection 15b. Pin 16 is movably positioned within elongated slot 15a so that the position of pin 16 in slot 15a changes as yoke shaft 10a rotates with main shaft 11. Projection 15b is coupled to the first articulation link. More than one articulation actuation mechanism may be provided to operate more than one articulation link.

Figure 18:
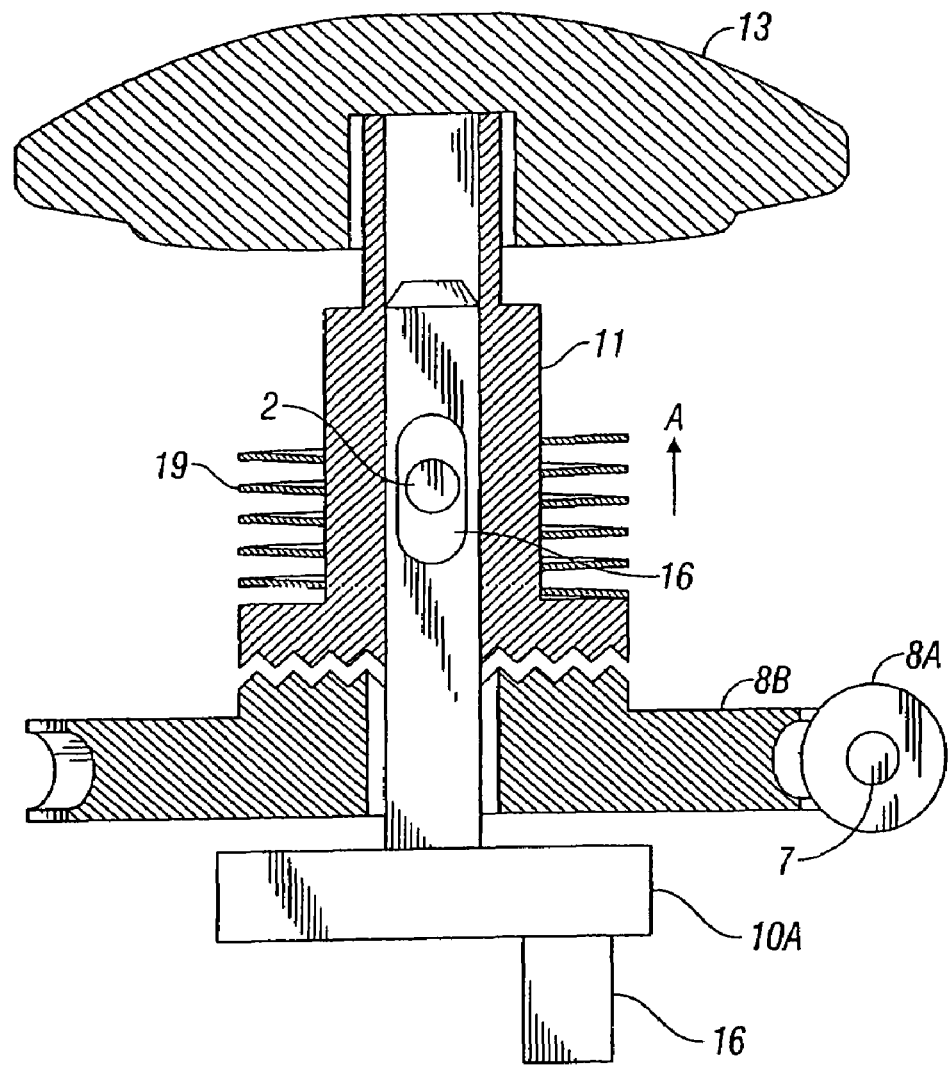
FIG. 18 is a cross-sectional view of an articulation mechanism according to an embodiment of the presently disclosed surgical stapling apparatus.

With reference to FIG. 18, in one embodiment, slip clutch 9 includes a shaft 10a having a pin 2. Pin 2 is slidably received in a slot 6 defined in main shaft 11. When the motor drives worm gear 8a, main shaft 11 is rotated, transferring the rotation to shaft 10a. When the clutch 9 slips (at the teeth), main shaft 11 moves upwardly, in the direction indicated by arrow "A," with respect to shaft 10. This allows manual operation of knob 13 and also prevents overloading of the motor assembly 5.

In a further embodiment, yoke shaft 10a is attached to, or integral with, second gear 8b. To avoid overloading motor assembly 5, a current sensor is used to shut down motor assembly 5 when the motor assembly 5 current reaches a predetermined limit or threshold.

In operation, when motor assembly 5 rotates transmission shaft 7, first gear 8a rotates and causes the rotation of second gear 8b. The rotation speed supplied by motor assembly 5 is reduced by the interaction of first and second gears 8a, 8b. Slip clutch 9 transfers the rotation of second gear 8a to main shaft 11. Main shaft 11, in turn, transfers its rotation to yoke shaft 10a. As yoke shaft 10a rotates, pin 16 moves within elongated slot 15a. The movement of pin 16 causes corresponding linear translation of J-channel 15 to advance the articulation link. The first articulation link moves axially in combination with the other structural elements discussed above to articulate tool assembly 17. When the limit of articulation is reached, or when a predetermined force is otherwise reached, slip clutch 9 will disengage, thus preventing a sudden stop of motor assembly 5. The disengagement of slip clutch 9 will produce an audible click to alert the operator that the articulation limit has been reached.

Alternatively, a user may articulate tool assembly 17 manually. A surgeon may manually rotate articulation knob 13. As articulation knob 13 rotates, slip clutch 9 disengages to prevent back driving motor assembly 5, and main shaft 11 moves upwardly with respect to yoke shaft 10a. The rotation of articulation knob 13 will also cause the corresponding rotation of the main shaft 11. Yoke shaft 10a rotates in response to the rotation of main shaft 11 to move pin 16. The motion of pin 16 along the length of elongated slot 15a causes the linear movement of J-channel 15. The translation of J-channel 15 advances the articulation link to articulate tool assembly 17. The connections between the switch 3 and power source 4 on the one hand, and the motor assembly 5 and gears 8a, 8b, J-channel 15, on the other, accommodate rotation of rotatable knob 28. By way of example, a circular sliding contact may be provided between battery pack 4 and switch 3 in the handle assembly 12 and the motor assembly 5 in the rotatable knob 28. In alternative embodiments, the knob 28 is omitted and the body 14 is fixed.

It will be understood that various modification may be made to the embodiments disclosed herein. Therefore, the above description should not be construed as limiting, but merely exemplifications of embodiments. For instance, the described surgical stapling apparatus 10 may be utilized in combination with a servomotor, position sensor, slide ring, electric brakes and electronic controls to add functions such as positioning articulation knob to its initial position, sensing limits of articulation with an automatic stop, among others. Those skilled in the art will envision other modification within the scope and spirit of the claims appended hereto.

What is claimed is:

1. A surgical stapling apparatus comprising:
    a handle assembly;
    an elongated body extending distally from the handle assembly;
    an articulation mechanism including:
        a first gear rotatably mounted on a transmission shaft and configured to engage a second gear;
        a clutch interconnecting the second gear and a main shaft; and
        a yoke shaft coupled to the main shaft and adapted to linearly advance a J-channel, the J-channel operatively connected to an articulation link.

2. The surgical stapling apparatus according to claim 1 further comprising a motor assembly operatively coupled to the transmission shaft.

3. The surgical stapling apparatus according to claim 2 further comprising a battery pack positioned on the handle assembly and connected to power the motor assembly.

4. The surgical stapling apparatus according to claim 2 further comprising a switch mounted on the handle assembly for activating the motor assembly.

5. The surgical stapling apparatus according to claim 1, wherein the yoke shaft includes a pin slidably secured on an elongated slot of the J-channel.

6. The surgical apparatus according to claim 1, wherein the J-channel includes a projection extending therefrom.

7. The surgical apparatus according to claim 1 further comprising an articulation knob mounted on the handle assembly and operatively connected to the main shaft.

8. A surgical stapling apparatus comprising:
    a handle assembly;
    an elongated body extending distally from the handle assembly;
    an articulation mechanism including:
        a motor assembly operatively coupled to a transmission shaft; and
        a first gear rotatably mounted on the transmission shaft and configured to engage a second gear;
        a clutch interconnecting the second gear and a main shaft;
        a yoke shaft coupled to the main shaft and adapted to linearly advance a J-channel.

9. The surgical stapling apparatus according to claim 8 further comprising a battery pack positioned on the handle assembly and electrically linked to the motor assembly.

10. The surgical stapling apparatus according to claim 8 further comprising a switch mounted on the handle assembly for activating and controlling the motor assembly.

11. The surgical stapling apparatus according to claim 8, wherein the yoke shaft includes a pin slidably secured on an elongated slot of the J-channel.

12. The surgical stapling apparatus according to claim 8, wherein the J-channel includes a projection extending therefrom.

13. The surgical stapling apparatus according to claim 8 further comprising an articulation knob mounted on the handle assembly and operatively connected to the main shaft.

14. The method of articulating a tool assembly of a surgical stapling apparatus comprising the steps of:
    providing an articulation mechanism including:
        a first gear rotatably mounted on a transmission shaft and configured to engage a second gear;
        a clutch interconnecting the second gear and a main shaft;
        a yoke shaft coupled to the main shaft and adapted to linearly advance a J-channel; and
    rotating the transmission shaft to articulate the tool assembly.

15. The method of articulating a tool assembly of a surgical stapling apparatus according to claim 14, wherein the step of rotating the transmission shaft is performed electromechanically.

16. The method of articulating a tool assembly of a surgical stapling apparatus comprising the steps of:
    providing an articulation mechanism including:
        a first gear rotatably mounted on a transmission shaft and configured to engage a second gear;
        a clutch interconnecting the second gear and a main shaft;
        a yoke shaft coupled to the main shaft and adapted to linearly advance a J-channel; and
    rotating the main shaft to articulate the tool assembly.

17. The method of articulating a tool assembly of surgical stapling apparatus according to claim 15, wherein the step of rotating the main shaft is performed manually.

* * * * *